(12) United States Patent
Licata et al.

(10) Patent No.: US 7,468,067 B2
(45) Date of Patent: Dec. 23, 2008

(54) ONE HAND TOURNIQUET WITH LOCKING MECHANISM

(75) Inventors: Mark Licata, Doswell, VA (US); Kevin R. Ward, Glen Allen, VA (US); Marcus E. Carr, Jr., Holland, PA (US)

(73) Assignees: Virginia Commonwealth University, Richmond, VA (US); Biotrack, LLC, Richmond, VA (US)

( * ) Notice: Subject to any disclaimer, the term of this patent is extended or adjusted under 35 U.S.C. 154(b) by 522 days.

(21) Appl. No.: 11/192,427

(22) Filed: Jul. 29, 2005

(65) Prior Publication Data

US 2006/0025807 A1    Feb. 2, 2006

Related U.S. Application Data

(60) Provisional application No. 60/591,957, filed on Jul. 29, 2004.

(51) Int. Cl.
*A61B 17/00* (2006.01)
*A44B 1/04* (2006.01)
*A44B 11/25* (2006.01)
*A44B 17/00* (2006.01)
*F16G 11/00* (2006.01)
*F16G 3/00* (2006.01)
*F16G 3/02* (2006.01)
*F16G 11/10* (2006.01)

(52) U.S. Cl. .......................... 606/203; 24/170; 24/323; 24/505

(58) Field of Classification Search .............. 606/203; 24/170, 311, 191, 635, 614, 615, 616, 278, 24/132 R, 133, 134 KB, 134, 132 AA, 68 R, 24/70 ST, 71 CT, 31 R, 32, 33 R, 307, 325, 24/327, 134 R, 323, 324, 505, 517, 625
See application file for complete search history.

(56) References Cited

U.S. PATENT DOCUMENTS

| 4,102,343 A | * | 7/1978 | Schneider | 606/203 |
| 4,125,115 A | * | 11/1978 | Mayo et al. | 606/203 |
| 4,516,576 A | * | 5/1985 | Kirchner | 606/203 |
| 5,084,062 A | * | 1/1992 | Sturm | 606/203 |

(Continued)

FOREIGN PATENT DOCUMENTS

EP    196646 A2 * 10/1986

*Primary Examiner*—Darwin P Erezo
*Assistant Examiner*—Naveen K Singh
(74) *Attorney, Agent, or Firm*—Whitham Curtis Christofferson & Cook, P.C.

(57) ABSTRACT

Provided is a tourniquet having two opposing and pivotally movable plates. The plates comprise a clamp that pinches an elastomeric cord. The plates are pivotally biased together by a spring. The cord is attached to a back end of the clamp. A free end of the cord is squeezed by the plates such that a loop of cord is provided. The cord can be pulled from the clamp to reduce the size of the loop. The clamp comprises a safety lock that prevents movement of the plates and slipping of the cord. The safety lock can comprise a button disposed between the plates in the back end of the clamp, preventing the plates from moving together in the back portion, and therefore from moving apart in a front portion that grips the cord. Also, the tourniquet clamp can comprise a dual-sided press connector mechanism for fast release of tourniquet tension.

6 Claims, 3 Drawing Sheets

U.S. PATENT DOCUMENTS

| | | | |
|---|---|---|---|
| 5,314,437 A | * | 5/1994 | Holtsch ....................... 606/157 |
| 5,511,288 A | * | 4/1996 | McAndrews et al. ........ 24/16 R |
| 6,192,554 B1 | * | 2/2001 | Dumcum .................. 24/16 PB |
| 2005/0113866 A1 | * | 5/2005 | Heinz et al. .................. 606/203 |
| 2005/0267518 A1 | * | 12/2005 | Wright et al. ............... 606/203 |

\* cited by examiner

ONE HAND TOURNIQUET WITH LOCKING MECHANISM

RELATED APPLICATIONS

The present application claims the benefit of priority from provisional application 60/591,947, filed on Jul. 29, 2004.

GOVERNMENT INTEREST

The development of the present invention was supported by the US Government under contract number OST 02-DH-08 from the US Special Forces. The Government has certain rights in the invention.

FIELD OF THE INVENTION

The present invention relates generally to tourniquet devices for blocking blood flow to an injured limb. More particularly, the present invention relates to a tourniquet device that can be applied, adjusted, and released with one hand.

BACKGROUND OF THE INVENTION

Tourniquet devices are commonly used in emergency medicine to stop blood flow to and bleeding from an injured limb. Tourniquets employ a length of cordage tightened around a limb to stop blood flow and allow clotting to occur. After a tourniquet is applied long enough to allow blood clotting or to stabilize the injury, in some cases the tourniquet can be slowly and partially released to prevent damage to the injured limb. It is important for tourniquets to maintain tension reliably; a sudden accidental release of tourniquet tension can result in significant loss of blood and renewed bleeding.

Sometimes it is necessary for an injured person to apply a tourniquet to himself. An injured person losing blood is weak and will be unable to apply a large force. Additionally, a person applying a tourniquet to himself typically will not have favorable leverage to apply force. Therefore, it is important in this case for the tourniquet to be settable with one hand and with a small amount of applied force. Also, the tourniquet should be able to be controllably loosened without unintentionally releasing the tourniquet pressure completely.

Tourniquets are essential in emergency medicine and are standard equipment for military and emergency medical personnel. Tourniquets sometimes need to be carried to remote areas and used in dirty outdoor conditions. For this reason, tourniquets should be small, durable, lightweight and reliable.

U.S. Pat. No. 4,125,115 to Mayo et al. describes a tourniquet employing a semi-elastic belt clamped between a jamming edge and a roller. The tourniquet of Mayo et al. does not provide a mechanism for locking tourniquet tension so that the tourniquet cannot be accidentally released. Mayo et al. has release mechanisms that can be easily triggered accidentally, resulting in sudden and complete loss of tourniquet tension. This is dangerous to injury victims, because sudden loss of the tourniquet can result in significant additional loss of blood.

It would be an advance in the art of emergency medicine and tourniquet design to provide a tourniquet that is reliably lockable and not prone to accidental release. It would also be beneficial to provide a tourniquet that can completely stop blood flow with a relatively small amount of applied force, so that an isolated single injured person can apply the tourniquet to himself.

SUMMARY

The present invention includes a one hand tourniquet having a tourniquet clamp. The tourniquet clamp has two pivotally mounted members, which may be plates, flat plates or other shapes. The members are biased together at a front end and biased apart at a back end. The members may be biased by a torsion spring, for example.

The tourniquet has an elastomeric cord. The elastomeric cord is secured to the back end, and passes between the members at the front end. The cord is therefore pinched between the members. Also included is a safety lock which prevents pivotal movement of the members when locking is desired.

The elastomeric cord can comprise a plurality of elastomeric cords. The elastomeric cords can be separately adjustable. Preferably, the elastomeric cords have a maximum elongation of at least 75%.

The safety lock can comprise a button that is insertable between the members in the back end. The safety lock will prevent the members from moving towards one another in the back end portion of the clamp. The button can comprise a U shape with flexible legs that allows it to be pressed through a hole in one of the members. The button preferably has steps that engage and lock with the hole, thereby preventing movement of the members.

Also, the tourniquet can comprise a dual sided press connector for rapidly releasing the tourniquet. The dual sided press connector can be attached to the back end of the tourniquet clamp.

DETAILED DESCRIPTION

The present invention provides a tourniquet that can be applied with one hand and requires only a small amount of force to completely stop blood flow. The present tourniquet comprises a pair of plates that are pivotally connected and biased together on a front end to form a clamp. The clamp allows elastomeric cord material to be pulled from the tourniquet such that the tourniquet is tightened. The tourniquet also includes a safety lock for preventing the plates from moving after the tourniquet has been set. Preferably, the safety lock comprises a button that jams the plates apart on a back side, thereby preventing the plates from moving apart on the front side. Additionally, the tourniquet may include a dual-sided press connector (e.g. similar to well known connectors sold under the trademarked names FASTEX™ or SIDE SQUEEZE™) for allowing rapid but accident-resistant release of the tourniquet.

Figure 1:
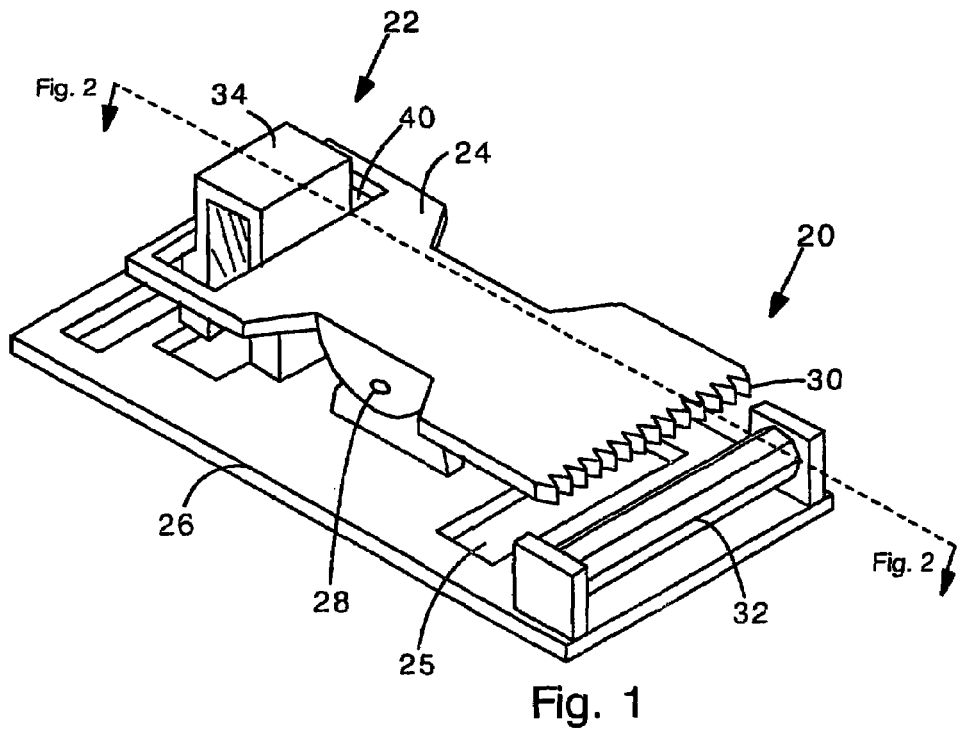
FIG. 1 shows a perspective view of the present tourniquet clamp.
Figure 2:
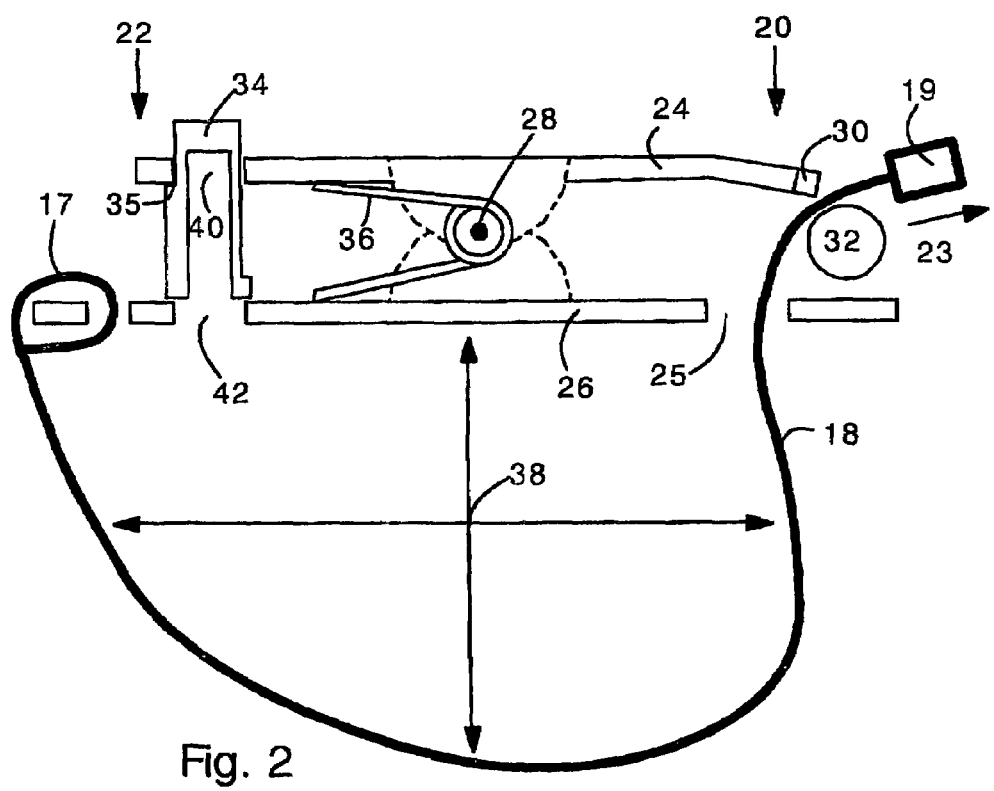
FIG. 2 shows a cross sectional side view of the tourniquet.

FIG. 1 shows a perspective view of the tourniquet clamp of the present invention. FIG. 2 shows a cross sectional side view of the clamp, in combination with a cord 18.

The clamp has a front end 20 and a back end 22. The clamp comprises a top plate or member 24 and a bottom plate or member 26. The plates are pivotally connected at pivot point 28. The top plate 24 has teeth 30 for grasping a cord 18 (not shown in FIG. 1) against a roller 32. The plates 24, 26 are urged by spring 36 such that the teeth 30 and the roller 32 are biased together. The spring 36 causes plates 24, 26 to be biased apart at the back end 22. As seen in FIG. 2, the cord is pinched between the teeth 30 and roller 32 due to the action of the spring 36. Preferably, the bottom plate 28 has a hole 25 for accommodating the cord 18. The cord has a portion 17 secured to the back end 22 of the clamp (e.g. by tying or sewing, for example). The cord 18 may have a handle 19 for grasping with one hand. The tourniquet has a loop area 38 for disposing around an injured limb.

In operation, the injured limb (not shown) is disposed in the loop area 38. The handle 19 is grasped and pulled. The clamp allows the loop area 38 to become smaller, but not larger. In other words, the clamp allows the cord 18 to pass between the teeth 30 and roller 32 in only one direction 23.

A benefit of the present invention is that only a small force applied to the handle will create a relatively high tension in the cord 18 and high compression in the loop area 38.

Preferably in the present invention, the cord is made of highly elastic material having a high capability for stretching. For example, the cord can be made of multifilamentary elastic material known by the tradename BUNGEE™ cord. The cord preferably has a capability of at least about 50%, 75%, 100%, or 150% elongation. High elasticity and elongation provides mechanical advantage for the user and therefore allows the user to more easily achieve high tension in the cord 18 and high compression in the loop area 38. The cord can comprise a single round or rectangular cord, or can comprise a wide strap similar in shape to webbing material. Alternatively, the cord can comprise several parallel round cords or wide straps, with each cord or strap having a separate handle 19. If several parallel cords are employed, then they can be tightened one cord at a time. One cord at a time tightening allows a weak user to achieve high tension in the cord (since tension is additive) and highly effective isolation of the injured limb. One cord at a time tightening will also provide high tension needed for isolating legs and other limbs that are difficult to isolate by tourniquet.

The plates 24, 26 can be made of stamped steel, molded plastic or other suitable materials. The roller 32 can also be made of plastic or metal.

A button 34 provides a safety lock mechanism. Button 34 is disposed between the plates 24, 26 at the back end 22. The button holds the plates 24, 26 apart in the back end, thereby preventing the plates 24, 26 from releasing their grip on the cord 18. The button 34 may have a step 35 on an external surface that engages hole 40 in the top plate. The step 35 holds up the top plate 24 and prevents it from moving toward the bottom plate 26, thereby assuring that the tourniquet clamp does not loosen.

Figure 3:
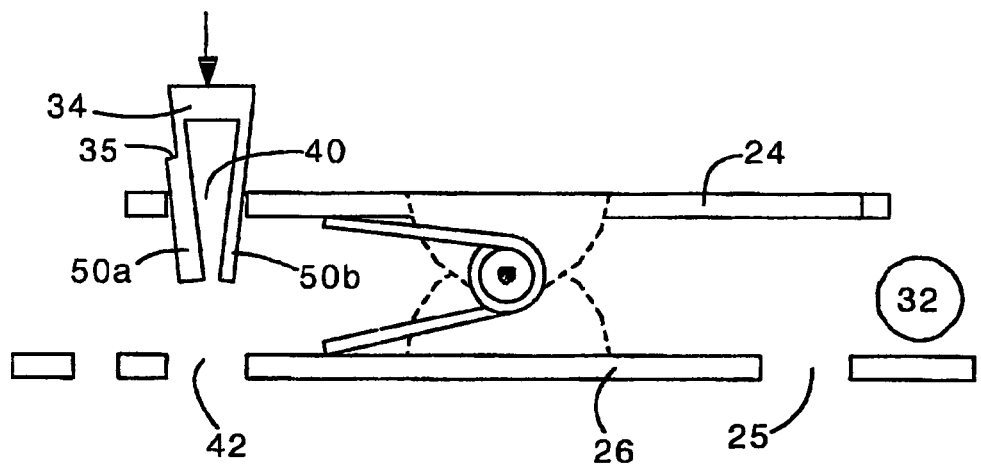
FIGS. 3 and 4 illustrate operation of the safety lock of the present tourniquet.
Figure 4:
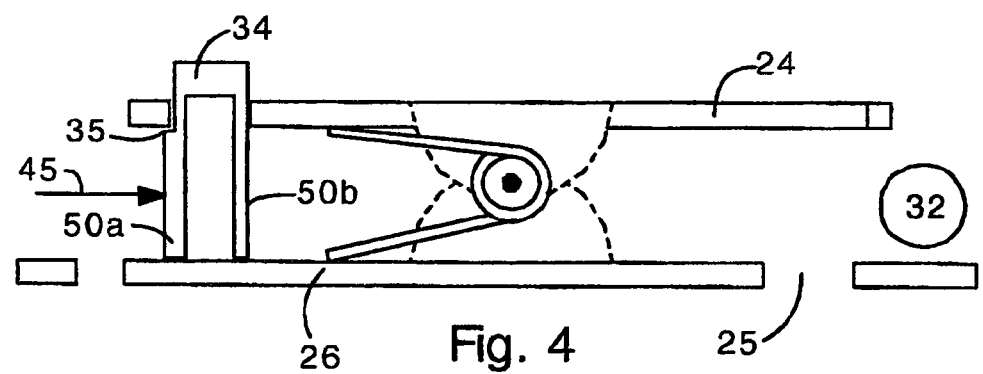

FIGS 3 and 4 illustrate insertion and usage of the safety lock button 34. Preferably, the safety lock button 34 has a U shape as shown. The U shape allows legs 50a, 50b of the button to be flexed by pressing together as illustrated in FIG. 3. When pressed together, the button 34 can be inserted through hole 40 in the top plate 24. When fully inserted, the legs 50a, 50b spring back to shape, and the top plate is immobilized by the step 35. The button 34 should have strength and resiliency so that the legs 50a, 50b are strong enough to withstand compressive forces for a long duration, and so that the legs 50a, 50b can flex to allow insertion of the button 34. The button 34 can be made of molded nylon or spring steel, for example.

In operation, the button 34 is inserted into the tourniquet clamp after the clamp has been tightened to its desired tension. The button 34 will lock the tourniquet clamp and not allow loosening of the tourniquet. However, in some embodiments, the tourniquet may be tightened further after insertion of the button 34.

Alternatively, the button 34 can be inserted through the hole 42 in the bottom plate 26. In this case the button is inserted into the clamp before it is applied to an injured limb.

In order to remove the button 34, and release the tourniquet, the leg 50a having the step 35 is pressed inwardly as illustrated by arrow 45 in FIG. 4. Then, the button can be pressed through the hole 42 or hole 40. Alternatively, both legs 50a, 50b are pressed together. The leg 50a must be pressed sufficiently such that the step 35 can pass through the hole 40.

It is noted that leg 50a, located toward the back end 22 should have a step 35; leg 50b, located toward the front end 20 may or may not have a step 35.

Hole 42 in bottom plate 26 is optional in the invention.

Figure 5:
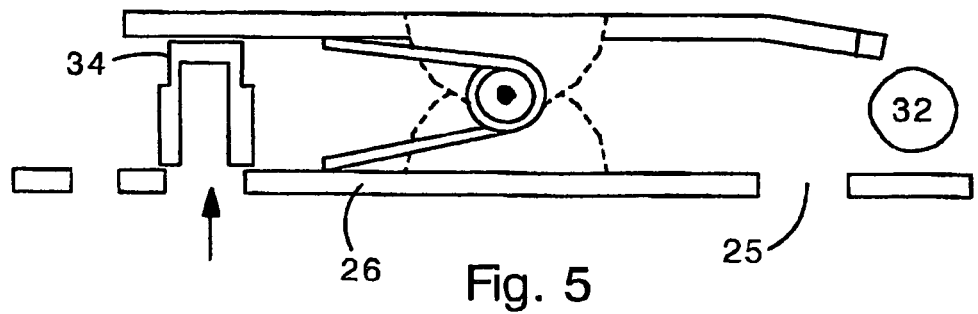
FIG. 5 shows an alternative embodiment in which a top plate of the tourniquet clamp does not have a hole for the safety lock button.

FIG. 5 shows an alternative embodiment in which the top plate 24 does not have hole 40. In this case, a top surface of button 34 presses against the top plate 24, thereby locking the tourniquet clamp.

Figure 6:
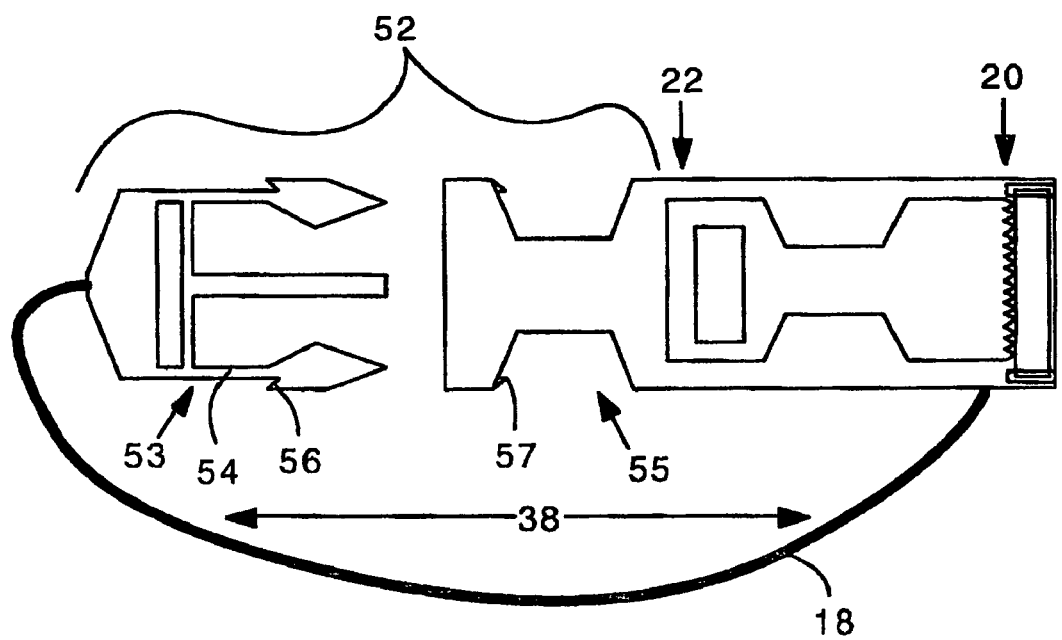
FIG. 6 illustrates an embodiment having a dual-sided press connector. The dual sided press connector is disconnected.
Figure 7:
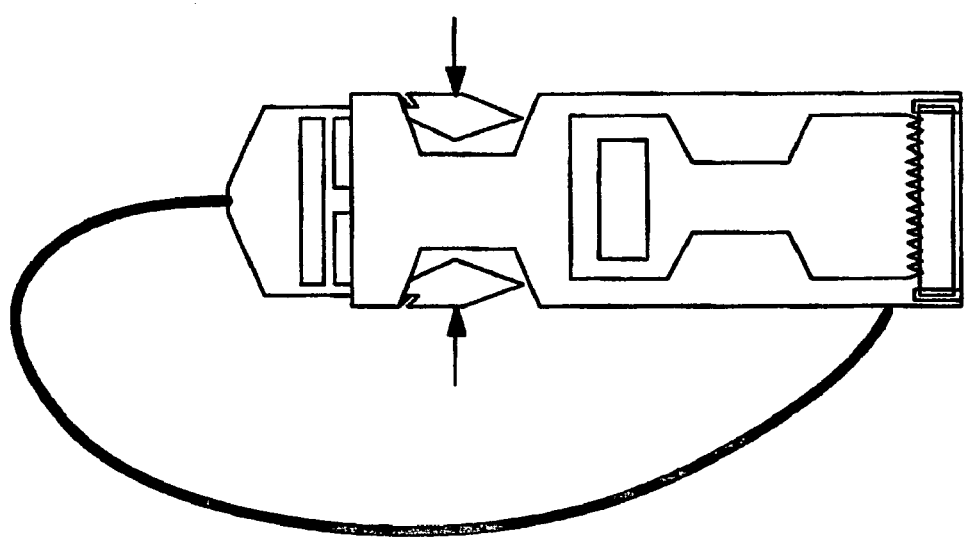
FIG. 7 illustrates an embodiment having a dual-sided press connector. The dual sided press connector is connected.

FIGS. 6 and 7 illustrate another embodiment of the invention in which a dual sided press connector 52 is used to attach the cord 18 to the clamp. In FIG. 6, the dual sided press connector is disconnected; in FIG. 7 the dual sided press connector is connected. Dual sided press connectors require a pressing action on both sides of the connector in order to release the mechanism, as illustrated in FIG. 7. In the embodiment of FIG. 6, the connector has a male portion 53 with flexible tongs 54 and barbs 56. A female portion 55 has edges 57 for engaging the barbs 56. However, it is noted that these features are not essential in the dual sided press connector. The present invention requires only that the connector be releasable by pressing from two opposing sides, as illustrated in FIG. 7. A connector that requires two-sided press action for release is unlikely to be accidentally released. This is a great benefit in emergency situations because the accidental release of a tourniquet can be dangerous as it allows further loss of blood. In a particular embodiment, the dual sided press connector is used in combination with the clip 34 embodiment illustrated in FIGS. 2-5.

Dual sided press connectors are well known in the art and commonly used in backpacks, luggage and the like. For example, U.S. Pat. No. 4,150,464 describes a dual sided press connector. Dual sided press connectors are commonly sold under the tradenames FASTEX™ and SIDE SQUEEZE™. Typically, dual sided press connectors are made from molded nylon or other polymers.

Although the present tourniquet clamp has been described as comprising plates, the invention is not so limited. The tourniquet clamp does not necessarily comprise plates or flat plates. The tourniquet clamp can comprise any curved or shaped members that are pivotally mounted to one another.

It will be clear to one skilled in the art that the above embodiment may be altered in many ways without departing from the scope of the invention. Accordingly, the scope of the invention should be determined by the following claims and their legal equivalents.

What is claimed is:

1. A one-hand operable tourniquet for medical applications, comprising:

a tourniquet clamp having two opposing pivotally movable members, wherein the members are biased together at a front end, and biased apart at a back end;

a cord having at least a portion secured to or securable to the back end of the tourniquet clamp and having a free end which passes between the two opposing movable members of the tourniquet clamp at the front end; and a safety lock which selectively prevents pivoting movement of the two opposing movable members when the free end of the cord is disposed between the two opposing movable members wherein the safety lock comprises a button insertable between the two opposing pivotally movable members in the back end of the tourniquet clamp, said button having at least a first portion which contacts a first of said two opposing pivotally movable members and at least a second portion which contacts a second of said two opposing pivotally movable members, whereby when said first portion and said second portion of said button respectively contact said first and second pivotally movable members said first and second pivotally movable members cannot pivot towards one another at said back end of said tourniquet clamp or away from each other at said front end of said tourniquet clamp, wherein one of said first and second pivotally movable members has a hole located at the back end of the tourniquet clamp, and the button has a U-shaped with legs that can be pressed together to fit through the hole and into a space between the two opposing pivotally movable members.

2. The one-hand operable tourniquet of claim 1 wherein cord comprises an elastic cord with a maximum stretch of at least 75%.

3. The one-hand operable tourniquet of claim 1, wherein the button has a step on an external surface which functions as said first or said second portion for respectively contacting said first and second pivotally movable members.

4. The one-hand operable tourniquet of claim 1 wherein said cord is secured to said tourniquet clamp by a dual sided press connector that can be released by releasing the dual sided press connector.

5. The one-hand operable tourniquet of claim 1 wherein one of the two opposing moveable members includes a roller element disposed at the front end, and over which the cord is pulled.

6. A one-hand operable tourniquet for medical applications, comprising:

a tourniquet clamp having two opposing pivotally movable members, wherein the members are biased together at a front end, and biased apart at a back end;

a cord having at least a portion securable to the back end of the tourniquet clamp and having a free end which passes between the two opposing movable members of the tourniquet clamp at the front end; and a dual-sided press connector for joining the portion of the cord to the back end of the tourniquet clamp, a safety lock which selectively prevents movement of the two opposing movable members when the free end of the cord is disposed between the two opposing movable members, and wherein the safety lock comprises a button insertable between the members in the back end that prevents the two opposing pivotally movable members from moving towards one another in the back end, and wherein one pivotally movable member has a hole in the back end of the tourniquet clamp, and the button has a U-shape with legs that can be pressed together to fit through the hole and into a space between the two opposing pivotally movable members to hold them apart at said back end of said tourniquet clamp.

* * * * *